US012721603B2

(12) United States Patent
Lee et al.

(10) Patent No.: US 12,721,603 B2
(45) Date of Patent: Sep. 1, 2026

(54) WEARABLE CARDIAC ULTRASOUND PATCH, CARDIOVASCULAR DISEASE IDENTIFICATION SYSTEM, AND METHOD THEREOF

(71) Applicant: National Cheng Kung University, Tainan City (TW)

(72) Inventors: Shuenn-Yuh Lee, Tainan City (TW); Chun-Rong Huang, Tainan City (TW); Ju-Yi Chen, Tainan City (TW); Meng-Dar Shieh, Tainan City (TW); Chih-Hsien Huang, Tainan City (TW); Ding-Siang Ciou, Kaohsiung City (TW); Yi-Ting Hsieh, Kaohsiung City (TW); Ming-Yueh Ku, Taichung City (TW); Kai-Ze Lei, Kaohsiung City (TW); Jia-Jun Liu, Tainan City (TW)

(73) Assignee: NATIONAL CHENG KUNG UNIVERSITY, Tainan City (TW)

( * ) Notice: Subject to any disclaimer, the term of this patent is extended or adjusted under 35 U.S.C. 154(b) by 0 days.

(21) Appl. No.: 18/978,524

(22) Filed: Dec. 12, 2024

(65) Prior Publication Data

US 2026/0144522 A1 May 28, 2026

(30) Foreign Application Priority Data

Nov. 28, 2024 (TW) ................................ 113146120

(51) Int. Cl.
*A61B 8/00* (2006.01)
*A61B 5/00* (2006.01)
(Continued)

(52) U.S. Cl.
CPC ............ *A61B 8/5207* (2013.01); *A61B 5/318* (2021.01); *A61B 5/6823* (2013.01); (Continued)

(58) Field of Classification Search
CPC ..... A61B 8/5207; A61B 5/318; A61B 5/6823; A61B 8/0883; A61B 8/4494; A61B 8/5269; A61B 2562/028
See application file for complete search history.

(56) References Cited

U.S. PATENT DOCUMENTS

2006/0253007 A1 * 11/2006 Cheng ................ A61B 5/14551 600/310

* cited by examiner

*Primary Examiner* — Keith M Raymond
*Assistant Examiner* — Adam D. Kolkin
(74) *Attorney, Agent, or Firm* — LANWAY IPR SERVICES; Chun-Ming Shih

(57) ABSTRACT

A wearable cardiac ultrasound patch, a cardiovascular disease identification system, and method thereof integrate a silicon photonic integrated circuit layer with a microelectromechanical integrated circuit layer into an optical fiber micro-sensor, which is encapsulated with a computing chip as a single unit. This allows the examinee to perform cardiac ultrasound detection and processing in a wearable and convenient manner, free from time or geographic constraints. The silicon photonic elements in the silicon photonic integrated circuit layer and the piezoelectric elements in the microelectromechanical integrated circuit layer are stacked and arranged in a two-dimensional array, enabling the wearable cardiac ultrasound patch to scan at more angles. Furthermore, the cardiovascular disease identification system of the present invention can process the examinee's cardiac ultrasound signals, electrocardiography (ECG) signals, and phonocardiography (PCG) signals. These three data types cross-validate one another, improving the detection rate of comprehensive cardiovascular diseases and reducing the time and misdiagnosis rate for physicians diagnosing cardiovascular diseases.

15 Claims, 8 Drawing Sheets

(51) Int. Cl.
*A61B 5/318* (2021.01)
*A61B 8/08* (2006.01)

(52) U.S. Cl.
CPC .......... *A61B 8/0883* (2013.01); *A61B 8/4494* (2013.01); *A61B 8/5269* (2013.01); *A61B 2562/028* (2013.01)

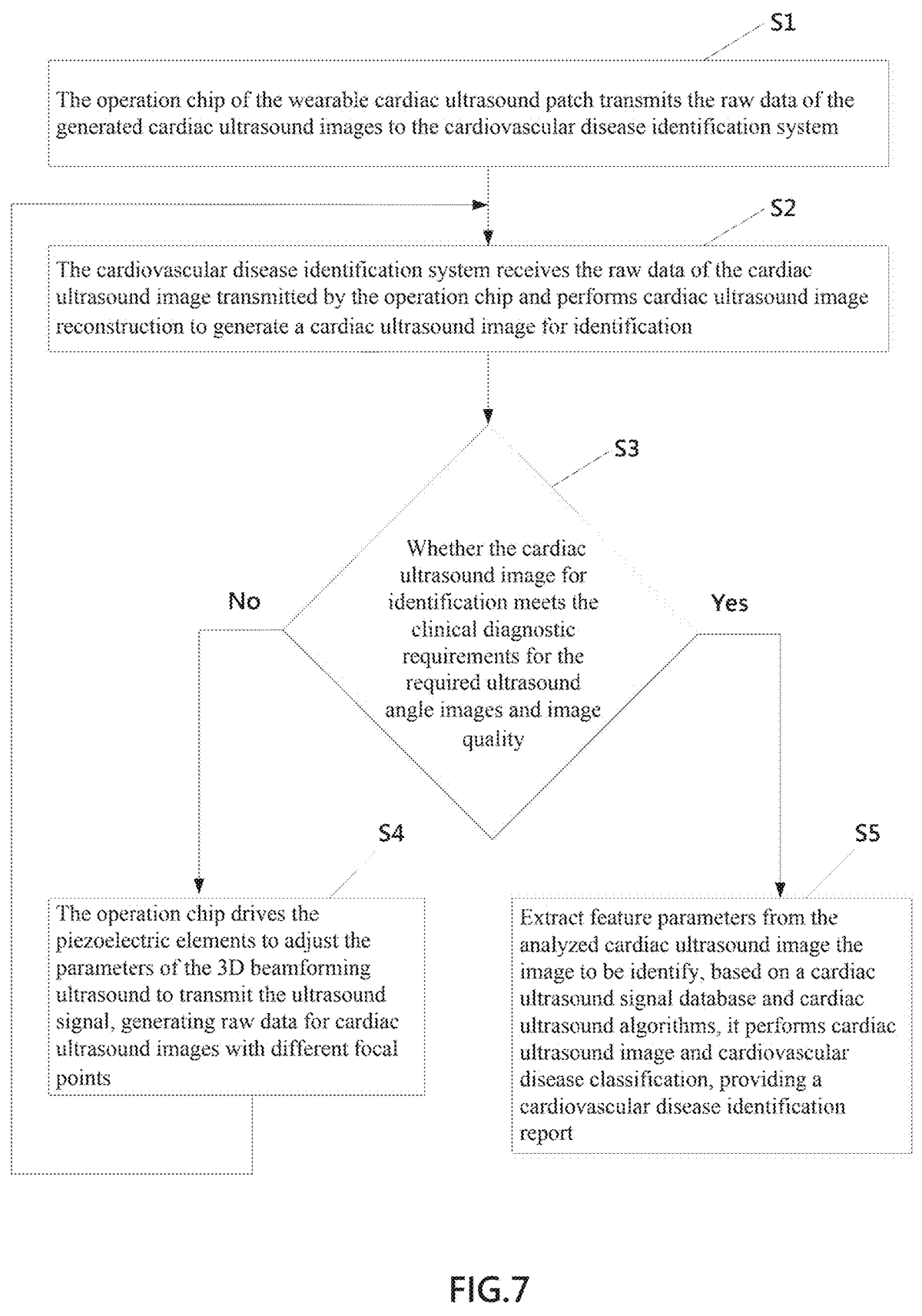

S1

The operation chip of the wearable cardiac ultrasound patch transmits the raw data of the generated cardiac ultrasound images to the cardiovascular disease identification system

S2

The cardiovascular disease identification system receives the raw data of the cardiac ultrasound image transmitted by the operation chip and performs cardiac ultrasound image reconstruction to generate a cardiac ultrasound image for identification

S3

Whether the cardiac ultrasound image for identification meets the clinical diagnostic requirements for the required ultrasound angle images and image quality No Yes

S4

The operation chip drives the piezoelectric elements to adjust the parameters of the 3D beamforming ultrasound to transmit the ultrasound signal, generating raw data for cardiac ultrasound images with different focal points

S5

Extract feature parameters from the analyzed cardiac ultrasound image the image to be identify, based on a cardiac ultrasound signal database and cardiac ultrasound algorithms, it performs cardiac ultrasound image and cardiovascular disease classification, providing a cardiovascular disease identification report

FIG.7

WEARABLE CARDIAC ULTRASOUND PATCH, CARDIOVASCULAR DISEASE IDENTIFICATION SYSTEM, AND METHOD THEREOF

CROSS-REFERENCE TO RELATED APPLICATIONS

This application claims the priority of Republic of China Patent Application No. 113146120 filed on Nov. 28, 2024, in the State Intellectual Property Office of the R.O.C., the disclosure of which is incorporated herein by reference.

BACKGROUND OF THE INVENTION

Field of the Invention

This invention relates to a wearable cardiac ultrasound patch, a cardiovascular disease identification system, and its method. More specifically, it is a wearable cardiac ultrasound patch, cardiovascular disease identification system, and its method that integrates a silicon photonic integrated circuit layer and a microelectromechanical integrated circuit layer into a fiber-optic micro-sensor, which is packaged with an computing chip as a unit to achieve cardiac ultrasound detection and processing.

Descriptions of the Related Art

With the advancement of medicine, the average life expectancy of people has increased, and the aging population has become an inevitable trend. As people age, physiological changes in the cardiovascular system occur, so older adults have a higher risk of cardiovascular disease. In addition, with the progress of the world economy and the acceleration of social pace, modern people's life pressures have increased sharply due to long working hours, leading to irregular lifestyles. Moreover, with advances in food technology and transportation, many processed foods and heavily seasoned foods have emerged. These lifestyle habits have significantly increased the incidence of modern cardiovascular diseases. Therefore, cardiac ultrasound is an important method for detecting cardiovascular diseases. Traditional cardiac ultrasound detection is a highly technical and time-consuming procedure, with expensive and scarce equipment and high demand for use. In many cases, domestic patients applying for cardiac ultrasound scans have to wait one to two months, and after the test, they must wait another one to two weeks to receive the diagnostic results. The lengthy diagnostic process easily causes delays in the optimal treatment window for cardiovascular diseases.

The existing method of cardiac ultrasound scanning involves high-technical measurement processing, and the training of personnel is difficult and in short supply. Moreover, the current cardiac ultrasound scanning technique relies on manual operation, where the technician must place the ultrasound probe at different positions on the patient's chest to avoid structures such as ribs and lungs, and find the optimal scanning angle to clearly display different parts of the heart. This typically involves multiple adjustments of the probe angle to obtain images from different sections. If the technician lacks sufficient experience in positioning and angle adjustments, additional shots are often required. Since the heart is constantly beating, the technician must simultaneously observe and capture key moments of heart activity, such as the images of the heart during systole and diastole. Therefore, the technician must have good technical and anatomical knowledge during the scanning process to ensure the clinical accuracy of the images. After the scan, the technician also needs to perform preliminary marking and measurements on the images, which include the size of the heart structures, wall thickness, chamber diameters, and so on, to provide reference for the physician's diagnosis.

As can be seen, the accuracy of the current cardiac ultrasound scanning largely depends on the technician's experience and technical skills. Furthermore, the generation of cardiovascular disease diagnostic reports requires a considerable amount of professional labor and time. Therefore, how to reduce the need for manual operation in cardiac ultrasound scanning and improve the efficiency of cardiac ultrasound detection has become an important issue.

SUMMARY OF THE INVENTION

In view of the drawbacks of the prior art mentioned above, the present application provides A wearable cardiac ultrasound patch for installing on the skin of the cardiac region to obtain cardiac images, the wearable cardiac ultrasound patch comprising: an encapsulation body, one side of which is equipped with an adhesive layer for attaching to the skin of the cardiac region; an optical fiber micro-sensor housed within the encapsulation body, the optical fiber micro-sensor comprising a silicon photonic integrated circuit layer with a plurality of silicon photonic elements arranged in a two-dimensional array and a microelectromechanical integrated circuit layer with multiple piezoelectric elements arranged in a two-dimensional array, and the silicon photonic integrated circuit layer and the microelectromechanical integrated circuit layer are vertically stacked, with each of the silicon photonic elements respectively corresponding to each of the piezoelectric element, and the silicon photonic integrated circuit layer is arranged facing the adhesive layer, and the microelectromechanical integrated circuit layer is used to emit ultrasonic waves and propagate them to the cardiac region, when ultrasonic echoes act on each of the piezoelectric elements and cause material deformation, the material deformation is captured by the silicon photonic elements and converted into phase changes of optical signal, and the silicon photonic integrated circuit layer then outputs the electrical signal converted from the optical signal; and an computing chip housed within the encapsulation body, vertically stacked with the optical fiber micro-sensor, wherein the computing chip employs 3D beamforming technology to drive the each of the piezoelectric elements to emit ultrasound, digitizes the electrical signal output by the silicon photonic integrated circuit layer, and performs AI-based data analysis, allowing ultrasound beams to focus on different angles and depths of the heart, thereby obtaining multi-angle ultrasound data and generating raw data of the cardiac ultrasound image.

Preferably, the wearable cardiac ultrasound patch said above, wherein the computing chip comprises: an ultrasonic transducer driver, supplying the required voltage and current to the plurality of piezoelectric elements of the microelectromechanical integrated circuit layer to control each of the piezoelectric elements to emit ultrasound; an analog front-end circuit, used to amplify the electrical signal output by the silicon photonic integrated circuit layer, perform noise suppression, and filter to reduce noise, quantizes the electrical signal into digital signal through analog-to-digital conversion; and a digital control system, receiving the digital signal processed by the analog front-end circuit, performing digital signal processing and data analysis to generate raw data of the cardiac ultrasound image, and storing the raw data for subsequent cardiac ultrasound image reconstruction.

Preferably, the wearable cardiac ultrasound patch said above, wherein the computing chip further comprises: a computation unit for performing AI computation, interpretation, and identification on the raw data of the cardiac ultrasound image generated by the digital control system, when the raw data the cardiac ultrasound image lacks effective data on cardiac structure, the information feeds back to the digital control system to control the ultrasonic transducer driver in adjusting the parameters of each piezoelectric element for emitting ultrasound, so that the raw data of the cardiac ultrasound image generated by the digital control system comprises effective data of the cardiac structure, reflecting the image of the cardiac region to achieve accuracy in the subsequent reconstruction processing of the cardiac ultrasound image.

Preferably, the wearable cardiac ultrasound patch said above, wherein the computing chip further comprises data transmission and storage functions for storing the raw data of the cardiac ultrasound image for subsequent reconstruction of the cardiac ultrasound image or transmitting the data to a cardiovascular disease identification system, and the cardiovascular disease identification system comprises a multi-angle identification network module and a cardiovascular disease detection network module, and the multi-angle identification network module stores multiple angle identification models for reconstructing the raw data of the cardiac ultrasound images to generate a cardiac ultrasound image to be identified and identifying the corresponding angle identification model to obtain the clinical diagnostic cardiac ultrasound perspective image and cardiac ultrasound image quality based on the cardiac ultrasound image to be identified, if the cardiovascular disease identification system determines that the cardiac ultrasound image to be identified does not meet the requirements of the cardiac ultrasound perspective image or cardiac ultrasound image quality, allowing the computing chip to drive each of the piezoelectric elements to adjust the ultrasound parameters of three-dimensional beamforming to emit ultrasound, thereby obtaining raw data of cardiac ultrasound images at different focal positions, and continue until the subsequently generated raw data produces a cardiac ultrasound image to be identified that meets the cardiac ultrasound perspective image and cardiac ultrasound image quality; the cardiovascular disease detection network module comprises a cardiac ultrasound signal database, which is used to analyze the cardiac ultrasound image to be identified that meets the cardiac ultrasound perspective image and cardiac ultrasound image quality, to extract feature parameters from the analyzed cardiac ultrasound image to be identified, and through the cardiac ultrasound signal database and cardiac ultrasound algorithm, performing cardiac ultrasound image and cardiovascular disease classification to provide a cardiovascular disease identification report.

The cardiovascular disease identification system of this application, which can perform data transmission processing with the wearable cardiac ultrasound patch of claim 1, wherein the computing chip of the wearable cardiac ultrasound patch comprises a data transmission function to transmit the raw data of the cardiac ultrasound image generated by the computing chip to the cardiovascular disease identification system, the cardiovascular disease identification system comprising: a multi-angle identification network module, configured to perform cardiac ultrasound image reconstruction processing on the raw data of the cardiac ultrasound image to generate a cardiac ultrasound image to be identified, wherein the multi-angle identification network module stores multiple view identification models, each of the view identification models comprises at least one cardiac ultrasound perspective image and corresponding cardiac ultrasound image quality, and identifies the corresponding view identification model based on the cardiac ultrasound image to be identified to obtain the cardiac ultrasound perspective image and cardiac ultrasound image quality required for clinical diagnosis, wherein if the cardiac ultrasound image to be identified does not meet the cardiac ultrasound perspective image or cardiac ultrasound image quality, the computing chip adjusts the three-dimensional beamforming ultrasound parameters to send ultrasound by driving each of the piezoelectric elements to obtain raw data of cardiac ultrasound images at different focal positions until the cardiac ultrasound image to be identified, obtained based on the subsequently generated raw data, meets the cardiac ultrasound perspective image and cardiac ultrasound image quality; and a cardiovascular disease detection network module, comprising a cardiac ultrasound signal database, configured to analyze the cardiac ultrasound image to be identified that meets the cardiac ultrasound perspective image and cardiac ultrasound image quality, extract feature parameters from the analyzed cardiac ultrasound image to be identified, and perform classification of the cardiac ultrasound image and cardiovascular diseases based on the cardiac ultrasound signal database and cardiac ultrasound algorithms to provide a cardiovascular disease identification report.

Preferably, the cardiovascular disease identification system said above, wherein the cardiovascular disease detection network module further comprises a heart sound signal database and receives sound signals generated by cardiac activities captured by a phonocardiography (PCG) detection device, analyzing and diagnosing the functionality and health condition of the heart based on the heart sound signal database.

Preferably, the cardiovascular disease identification system said above, wherein the cardiovascular disease detection network module further comprises an electrocardiography (ECG) signal database and receives electrocardiographic signals detected by an electrocardiography detection device, monitoring heart rhythms and diagnosing heart-related diseases based on the electrocardiography signal database.

The cardiovascular disease identification method of this application, applying the wearable cardiac ultrasound patch said above and a cardiovascular disease identification system to perform data transmission processing to achieve cardiovascular disease identification, the cardiovascular disease identification method comprising the following steps: (1) the computing chip of the wearable cardiac ultrasound patch transmits the raw data of the generated cardiac ultrasound image to the cardiovascular disease identification system; (2) the cardiovascular disease identification system receives the raw data of the cardiac ultrasound image transmitted from the computing chip and performs cardiac ultrasound image reconstruction processing to generate a cardiac ultrasound image to be identified; (3) the cardiovascular disease identification system determines whether the cardiac ultrasound image to be identified meets the cardiac ultrasound perspective image and cardiac ultrasound image quality required for clinical diagnosis, if the cardiac ultrasound image to be identified does not meet the cardiac ultrasound perspective image or cardiac ultrasound image quality, the computing chip adjusts the three-dimensional beamforming ultrasound parameters to send ultrasound by driving each of the piezoelectric elements to obtain raw data of cardiac ultrasound images at different focal positions until the cardiac ultrasound image to be identified, obtained based on the subsequently generated raw data, meets the cardiac ultrasound perspective image and cardiac ultrasound image quality; and (4) the cardiovascular disease identification system analyzes the cardiac ultrasound image to be identified that meets the cardiac ultrasound perspective image and cardiac ultrasound image quality, extracts feature parameters from the analyzed cardiac ultrasound image to be identified, and performs classification of the cardiac ultrasound image and cardiovascular diseases based on the cardiac ultrasound signal database and cardiac ultrasound algorithms to provide a cardiovascular disease identification report.

Preferably, the cardiovascular disease identification method said above, wherein before performing step (1), the method further comprises the following steps: (1-1) the computing chip of the wearable cardiac ultrasound patch interprets the raw data of the generated cardiac ultrasound image; (1-2) the computing chip analyzes whether the interpreted raw data of the cardiac ultrasound image contains effective data of cardiac structures, wherein if it does not contain effective data of cardiac structures, proceed to step (1-3), and if it does, proceed to step (1-4); (1-3) if the computing chip determines that the raw data of the cardiac ultrasound image does not contain effective data of cardiac structures, the computing chip adjusts the ultrasound emission parameter of each of the piezoelectric elements to ensure that the subsequent raw data of the cardiac ultrasound image generated by the computing chip contains effective data of the cardiac structure, and then proceed to step (1); and (1-4) if the computing chip determines that the raw data of the cardiac ultrasound image contains effective data of cardiac structures, proceed to step (1).

In summary, the wearable cardiac ultrasound patch, cardiovascular disease identification system, and method thereof of the present invention integrate the silicon photonic integrated circuit layer and the microelectromechanical integrated circuit layer into a optical fiber micro-sensor, which is encapsulated with a computing chip into a single unit. This allows the subject to perform cardiac ultrasound detection processing conveniently in a wearable manner according to their needs. Each of the silicon photonic elements in the silicon photonic integrated circuit layer and each of the piezoelectric elements in the microelectromechanical integrated circuit layer are stacked and arranged in a two-dimensional array, enabling the wearable cardiac ultrasound patch to scan at more angles. For piezoelectric micromachined ultrasonic transducers (pMUT), the reception of ultrasound originates from the deformation of the piezoelectric layer caused by the vibration of the membrane. The wearable cardiac ultrasound patch of the present invention employs silicon photonic technology to detect membrane vibrations, thereby improving the sensitivity issues of piezoelectric materials in signal reception. Additionally, leveraging the advantages of silicon photonic technology, comprising low noise, high speed, and high sensitivity, the driving voltage required is reduced. Consequently, the wearable cardiac ultrasound patch of the present invention operates with lower power consumption. Furthermore, the cardiovascular disease identification system of the present invention can detect the subject's cardiac ultrasound, electrocardiographic signals, and heart sound signals, process these signals to obtain cardiovascular disease-related parameters, and input them into artificial intelligence-based cardiovascular disease identification and diagnostic algorithms for disease classification. This comprises cardiovascular conditions such as cardiac valve disease, heart failure, coronary artery disease, and arrhythmias, thereby reducing the time and misdiagnosis rates for physicians diagnosing cardiovascular diseases.

BRIEF DESCRIPTION OF THE DRAWINGS

The above and other aspects, features and other advantages of the present invention will be more clearly understood from the following detailed description taken in conjunction with the accompanying drawings, in which:

FIG. 7 is a flowchart illustrating the processing steps of the cardiovascular disease identification method of the present invention.

DETAILED DESCRIPTION OF THE PREFERRED EMBODIMENT

Embodiments of the present invention will now be described in detail with reference to the accompanying drawings. The invention may, however, be embodied in many different forms and should not be construed as being limited to the embodiments set forth herein. Rather, these embodiments are provided so that this disclosure will be thorough and complete, and will fully convey the scope of the invention to those skilled in the art.

The cardiac ultrasound image detection and processing provided by the wearable cardiac ultrasound patch of this invention reduce the tedious processes of traditional cardiac ultrasound measurement. Moreover, the detection and processing are not limited by environmental or time constraints. Through the cardiovascular disease identification system of this invention, real-time identification and prediction of cardiovascular diseases can be performed to assist physicians in diagnosis, enabling them to obtain measurement reports in a shorter time, thereby improving medical quality. Additionally, it can be applied to telemedicine, offering a more convenient and efficient method for measuring cardiovascular diseases.

Figure 1:
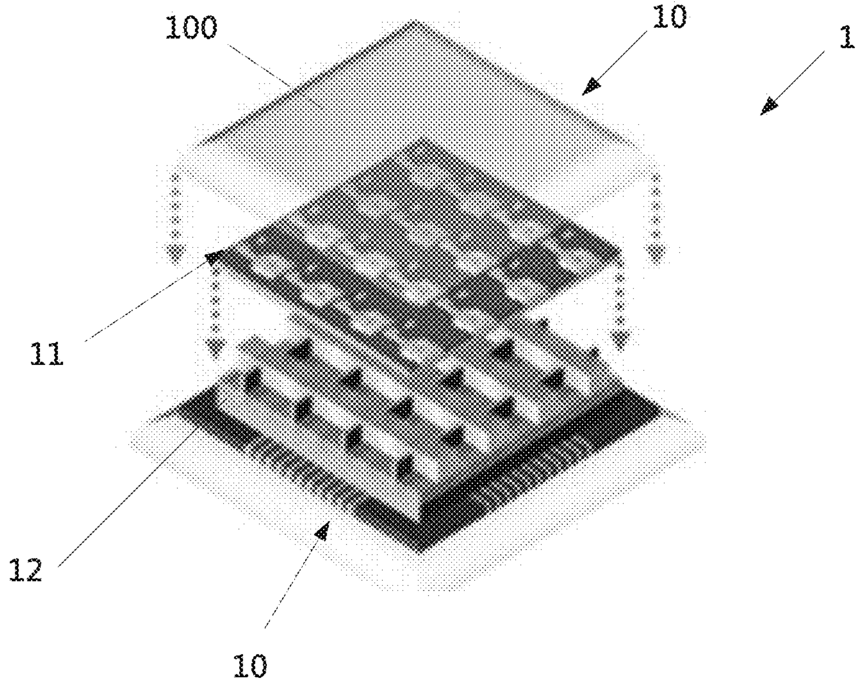
FIG. 1 is a structural exploded view of the wearable cardiac ultrasound patch of the present invention.
Figure 2:
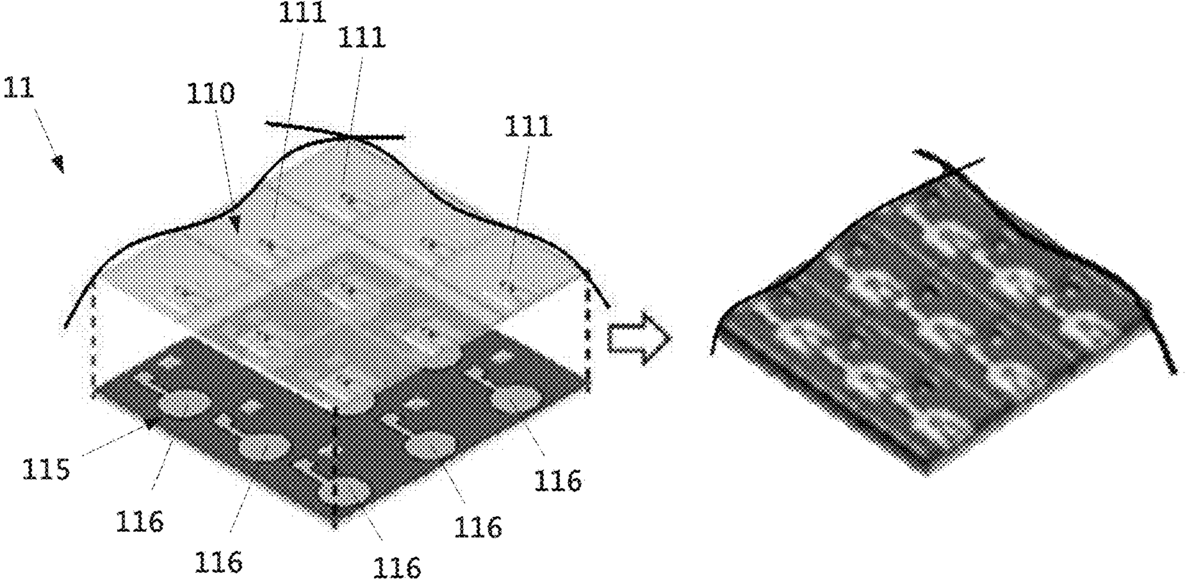
FIG. 2 is a structural diagram of the optical fiber micro-sensor in the wearable cardiac ultrasound patch of the present invention.

First, as shown in FIG. 1, which is an exploded structural diagram of the wearable cardiac ultrasound patch 1 of this invention, the wearable cardiac ultrasound patch 1 is used to be attached to the skin of the cardiac area, specifically on the slightly left part of the chest, to capture cardiac images. The wearable cardiac ultrasound patch 1 comprises an encapsulation body 10, an optical fiber micro-sensor 11, and a computing chip 12. The encapsulation body 10 is used to encapsulate the optical fiber micro-sensor 11 and the computing chip 12. Please also refer to FIG. 2, which is a structural diagram of the optical fiber micro-sensor 11. The optical fiber micro-sensor 11 comprises a silicon photonic integrated circuit layer 110 composed of a plurality of silicon photonic elements 111 arranged in a two-dimensional array, and a microelectromechanical integrated circuit layer 115 composed of a plurality of piezoelectric elements 116 arranged in a two-dimensional array. The silicon photonic integrated circuit layer 110 and the microelectromechanical integrated circuit layer 115 are vertically stacked, with each of the silicon photonic elements 111 corresponding to each of the piezoelectric elements 116. The computing chip 12 is vertically stacked with the optical fiber micro-sensor 11 and is electrically connected to the silicon photonic elements 111 and the piezoelectric elements 116.

One side of the encapsulation body 10 is equipped with an adhesive layer 100 for adhering to the skin of the cardiac area. The silicon photonic integrated circuit layer 110 faces the adhesive layer 100. The piezoelectric elements 116 of the microelectromechanical integrated circuit layer 115 emit ultrasound that propagates to the cardiac area. When ultrasound echoes act on the piezoelectric elements 116, causing material deformation, the material deformation is captured by the silicon photonic element 111 and converted into phase changes in optical signals. In other words, phase variations of the ultrasound are mapped into phase modulation of light waves via the piezoelectric effect and the sensitivity of optical elements, thereby transforming the deformation into optical signals that reflect changes induced by the ultrasound.

The computing chip 12 uses three-dimensional beamforming (3D beamforming) technology to control each of the piezoelectric elements 116 on the microelectromechanical integrated circuit layer 115 to emit ultrasound. It also digitizes the electrical signals output by the silicon photonic integrated circuit layer 110 and performs artificial intelligence data analysis. By analyzing the intensity of reflected waves and the echo time, different tissue densities and their distances from the optical fiber micro-sensor 11 can be determined. In cardiac ultrasound examination, the frequency of ultrasound is closely related to its penetration depth and image resolution. Low-frequency ultrasound (approximately 2-5 MHz) comprises strong penetration and is suitable for observing deeper structures, such as the deep structures of an adult heart. Low-frequency wavelengths are longer, making them more capable of penetrating the body's tissues without being quickly absorbed, allowing clear images to be obtained from deeper areas. Wavelengths of high-frequency are shorter, and although they provide higher resolution, their energy is more easily absorbed by the body's tissues, resulting in a reduced penetration depth. As previously mentioned, due to the close relationship between the frequency of ultrasound, its penetration depth, and image resolution, the wearable cardiac ultrasound patch 1 of this invention automatically adjusts the frequency of ultrasound emitted by each of the piezoelectric elements 116 via the computing chip 12. This allows ultrasound beams to focus on different angles and depths of the heart, capturing ultrasound data from multiple angles and generating raw data of cardiac ultrasound images.

The microelectromechanical integrated circuit layer 115 utilizes piezoelectric effect technology, such as piezoelectric microelectromechanical ultrasonic transducers (pMUTs), to convert electrical energy into mechanical vibrations that emit ultrasound and receive reflected ultrasound echoes from tissues or structures of different densities (e.g., heart muscle, heart chambers, and blood). The silicon photonic integrated circuit layer 110 detects the ultrasonic echo-induced minute material deformation of structures such as optical resonators or optical waveguides (which are not illustrated here) in the silicon photonic integrated circuit layer 110, based on the detection principle of optical mechanical vibrations from, for example, an optical micro-machined ultrasound sensor (OMUS), converting the deformation into a change in optical signal. These deformations alter the transmission path or phase of optical signals, leading to interference or frequency changes in optical signals, these optical changes represent received sound wave characteristics. This optical modulation technique combines silicon photonics technology to transmit optical signals, so that the ultrasonic echoes are optically processed inside the optical micro-machined ultrasound sensor into high-precision, low-noise data, making it easier for further analysis. The silicon photonic element 111 precisely modulates the phase or intensity of optical signals, aiding in the identification of the relative strengths and time differences in ultrasound echoes, producing high-resolution signal outputs. This technology can store echo information at different levels as optical phase information, and after being converted into an electrical signal, it is provided to the computing chip 12 for digitization and generating the raw data of the cardiac ultrasound image required for subsequent heart image reconstruction. Additionally, optical signal processing via the silicon photonic elements 111 enhances the sensitivity and accuracy of ultrasound sensing, reduces susceptibility to external electromagnetic interference (EMI), and significantly improves the signal-to-noise ratio, eliminating performance issues faced by traditional electronic sensors in medical environments.

Therefore, the wearable cardiac ultrasound patch 1 of this invention is an ultrasound sensing technology integrating silicon photonics and microelectromechanical systems, primarily leveraging optical resonance and mechanical vibration to detect ultrasound signals. The sensor operates based on the correlation between wavelength shifts in optical resonators and mechanical deformation. When ultrasound signals strike the membrane or structure of the sensor, they cause changes in the optical path, reflected in the variations of optical signals, achieving precise ultrasound measurement. It is particularly noted that the silicon photonic integrated circuit layer 110 comprises a photodetector (e.g., photodiode), typically located adjacent to or beneath the silicon photonic elements 111, to instantly detect optical signals modulated within the silicon photonic elements 111. These optical signals are ultimately detected by a photodetector and converted into an electrical signal, which is transmitted to the computing chip 12 for digitization and the generation of raw data for cardiac ultrasound image required for subsequent heart image reconstruction.

To facilitate the use of the wearable cardiac ultrasound patch of this invention by examinees, such that the examinees do not need to specifically ensure that the wearable cardiac ultrasound patch is precisely installed at a specific position on the skin over the cardiac region, the computing chip 12 of the wearable cardiac ultrasound patch 1 performs position calibration. Specifically, when the computing chip 12 first drives each of the piezoelectric elements 116 to emit ultrasound, it conducts an initialization process to calibrate the position of the encapsulation body 10 relative to the cardiac region. It is worth noting that the computing chip 12 is preloaded with multiple identification data for cardiac detection zone positioning and the corresponding ultrasound control parameters for each of these identification data. The cardiac detection zone positioning at least comprises: the parasternal region, apical region, and subcostal region. Therefore, the computing chip 12 can control the parameters of ultrasound emission by each of the piezoelectric elements 116 according to different cardiac detection zone position. The judgment of the cardiac detection zone is based on the raw data of the initial cardiac ultrasound image generated by the computing chip 12, and the raw data primarily originates from the sound wave signals of ultrasound reflections. These sound wave signals of ultrasound reflections comprise the echo characteristics (e.g., reflection intensity, echo delay) of tissues at various depths, providing a digitized representation of the structural and tissue density characteristics of the cardiac region. Based on the determined structural and tissue density characteristics of the cardiac region, the wearable cardiac ultrasound patch 1 identifies its applied position, determines the cardiac detection zone for this position, and locates the identification data and corresponding ultrasound control parameters for that zone. After the position calibration by the computing chip 12, the confirmed cardiac detection zone is used to adjust the waveforms and wavelengths of the ultrasound generated by each of the piezoelectric elements 116. This ensures the ultrasound beams are focused on the correct angles and depths of the heart.

Figure 3:
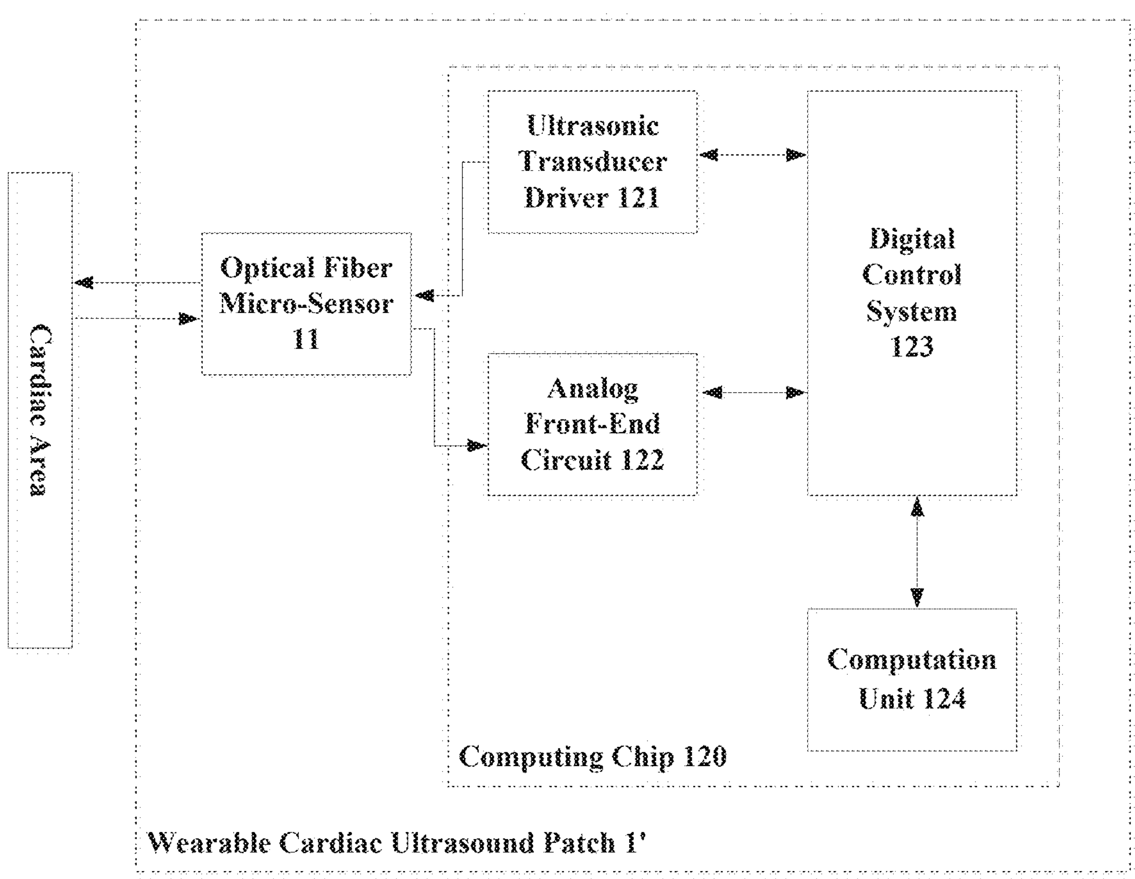
FIG. 3 is a basic block diagram of an embodiment of the computing chip in the wearable cardiac ultrasound patch of the present invention.

Refer to FIG. 3, which shows a basic structural block diagram of an embodiment of the computing chip in the wearable cardiac ultrasound patch. In this embodiment, the computing chip 120 comprises: an ultrasound transducer driver 121, an analog front-end (AFE) circuit 122, a digital control system 123, and a computation unit 124. Additionally, refer to FIGS. 1 and 2, the ultrasonic transducer driver 121 is used to provide the voltage and current required to the multiple piezoelectric elements 116 of the microelectromechanical integrated circuit layer 115 of the optical fiber micro-sensor 11, thereby driving the multiple piezoelectric elements 116 of the microelectromechanical integrated circuit layer 115 of the optical fiber micro-sensor 11, which is attached to the skin in the cardiac region. The multiple piezoelectric elements 116 generate corresponding ultrasounds according to the driving parameters. These ultrasounds encounter tissues or structures of different densities (e.g., heart muscle, cardiac chambers, and blood) and reflect upon contact. The ultrasound transducer driver 121 adjusts ultrasound parameters, such as frequency, based on the depth and resolution requirements of the cardiac detection. Lower frequency signals penetrate deeper tissues but have lower resolution, while higher frequencies are more suitable for shallow tissue detection with higher resolution. When the reflected waves reach the piezoelectric elements 116, the piezoelectric elements 116 cause slight deformations because of the effect of waves. At this point, the silicon photonic elements 111 on the silicon photonic integrated circuit layer 110 of the optical fiber micro-sensor 11 are respectively affected by the piezoelectric deformations of the each of the piezoelectric elements 116. These deformations further influence the optical structures (such as optical resonators or optical waveguides) within the silicon photonic elements 111, causing the optical signals to be modulated according to the deformations, thereby outputting electrical signals.

The analog front-end circuit 122 amplifies the electrical signals converted by the silicon photonic elements 111 in the silicon photonic integrated circuit layer 110. It also suppresses noise and performs filtering to reduce interference, ensuring signal quality. This facilitates more precise processing for image reconstruction in the subsequent digital control system 123, and analog-to-digital conversion quantifies the electrical signals into digital signals.

The digital control system 123 receives the digital signals processed by the analog front-end circuit 122, performing digital signal processing (DSP) and data analysis to generate raw data for cardiac ultrasound image. The raw data is stored for subsequent cardiac ultrasound image reconstruction. In this invention, the wearable cardiac ultrasound patch 1' preprocesses data to generate raw data for cardiac ultrasound image. For high-resolution cardiac ultrasound images, reconstruction is handled by a back-end device (e.g., a remote server), which will be elaborated on in FIG. 4. Therefore, the digital control system 123 further comprises a data transmission function to externally transmit the generated raw data of the cardiac ultrasound images. This data can be remotely sent to the aforementioned back-end equipment or locally transmitted to information processing devices such as mobile phones or computers. The back-end equipment or information processing devices can perform cardiac ultrasound image reconstruction and classify the cardiac ultrasound images and cardiovascular diseases. This allows medical personnel to promptly identify any abnormalities or potential risks in the subject's heart based on the cardiac ultrasound images and to take appropriate measures in emergency situations.

To ensure the raw data of the cardiac ultrasound image reconstruction by back-end equipment or information processing devices is valid, the computation unit 124 of the computing chip 120 in the wearable cardiac ultrasound patch 1' can perform AI operations, interpretation, and identification on the raw data of the cardiac ultrasound image generated by the digital control system 123. If it identifies the raw data of the cardiac ultrasound image lacking effective heart structure information, feedback is sent to the digital control system 123 to adjust the ultrasound frequency and focusing methods of each of the piezoelectric element 116 via the ultrasound transducer driver 121. This ensures that the raw data of the cardiac ultrasound image generated by the digital control system 123 contains effective heart structure information, guaranteeing the accuracy of the cardiac ultrasound image reconstruction by back-end equipment. Therefore, the computation unit 124 functions similarly to an edge computing device, pre-analyzing the validity of raw data of the cardiac ultrasound image before it is provided to back-end equipment or information processing devices, reducing their computational load. Additionally, the computation unit 124 provides auxiliary computational and management functions beyond the digital control system 123. Based on the current detection requirements, it adjusts the power, frequency, and focusing methods of the ultrasound transducer driver 121 dynamically according to the examinee's heart characteristics, enhancing diagnostic accuracy.

To optimize ultrasound parameter adjustments for personalized detection services tailored to the unique characteristics of each examinee's heart while maintaining diagnostic accuracy, the wearable cardiac ultrasound patch of this invention, with its data transmission capabilities, can transmit the raw data generated by the computing chip 120 to an information processing device for cardiac ultrasound image reconstruction. The computing chip 120 can also receive control information from the information processing device, comprising adjustments to the power, frequency, and focusing methods of the ultrasound transducer driver 121. Conversely, the information processing device is equipped with a built-in cardiovascular disease identification application. This application provides a user interface, allowing users (e.g., medical personnel) on the information processing device to view the reconstructed cardiac ultrasound images through the interface. If the user is dissatisfied with the quality of the cardiac ultrasound images, they can input the desired viewing angle via the user interface. The cardiovascular disease identification application retrieves the ultrasound parameters corresponding to the specified viewing angle and transmits them to the wearable cardiac ultrasound patch. The computation unit 124 then adjusts the power, frequency, and focusing mode of the ultrasonic transducer driver 121 according to these ultrasound parameters. In summary, the interactive architecture between the wearable cardiac ultrasound patch and the aforementioned information processing or backend equipment is based on the design principles of the internet of things (IoT). This enables seamless data exchange, achieving functionalities such as remote control and status monitoring. Therefore, the wearable cardiac ultrasound patch described in this invention can be applied to telemedicine, offering a more convenient and efficient method for cardiovascular disease assessment.

Figure 4:
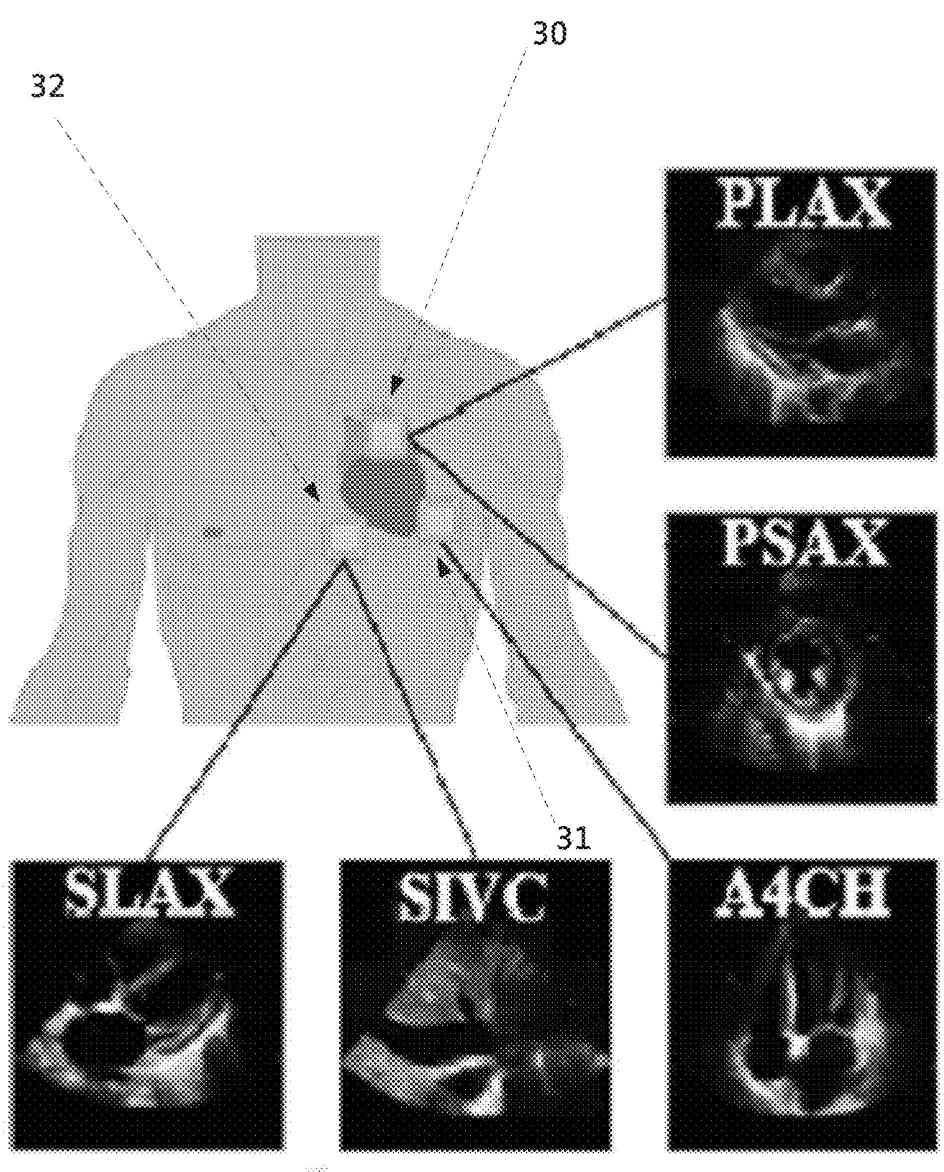
FIG. 4 is an application example of the wearable cardiac ultrasound patch of the present invention.

It is particularly noted that the wearable cardiac ultrasound patch of this invention can be used individually, and the number of patches can be increased or decreased for extended applications. The more patches used, the more comprehensive and complete the captured cardiac ultrasound images become. Therefore, using more patches improves the detection range and accuracy. In this embodiment, three wearable cardiac ultrasound patches are used for detection, as shown in FIG. 4. Each of the wearable cardiac ultrasound patches is affixed to one of the following regions: the parasternal region 30, the apical region 31, and the subcostal region 32. This configuration allows each patch to cover an emission range of 120 degrees, achieving 360-degree cardiac ultrasound imaging. The position of the wearable cardiac ultrasound patches and the ultrasound emission angles of their internal piezoelectric materials determine the image's viewing angle and structural visibility. When the three patches are arranged as illustrated in FIG. 4 for cardiac ultrasound detection, the following imaging views can be obtained: the parasternal long axis view (PLAX), the parasternal short axis view (PSAX), the apical four-chamber view (A4CH) observing the heart from the apex, the subcostal inferior vena cava view (SIVC) observing the inferior vena cava (IVC) from the subcostal (xiphoid) region, and the subcostal long axis view (SLAX) capturing the overall heart structure from the xiphoid position. By controlling the ultrasound parameters of each of the piezoelectric elements 116 within the microelectromechanical integrated circuit layer 115, the ultrasound beams can be focused on different angles and depths of the heart. This generates multi-angle ultrasound data and captures multiple cardiac ultrasound images, providing physicians with diagnostic information for various cardiovascular diseases.

Figure 5:
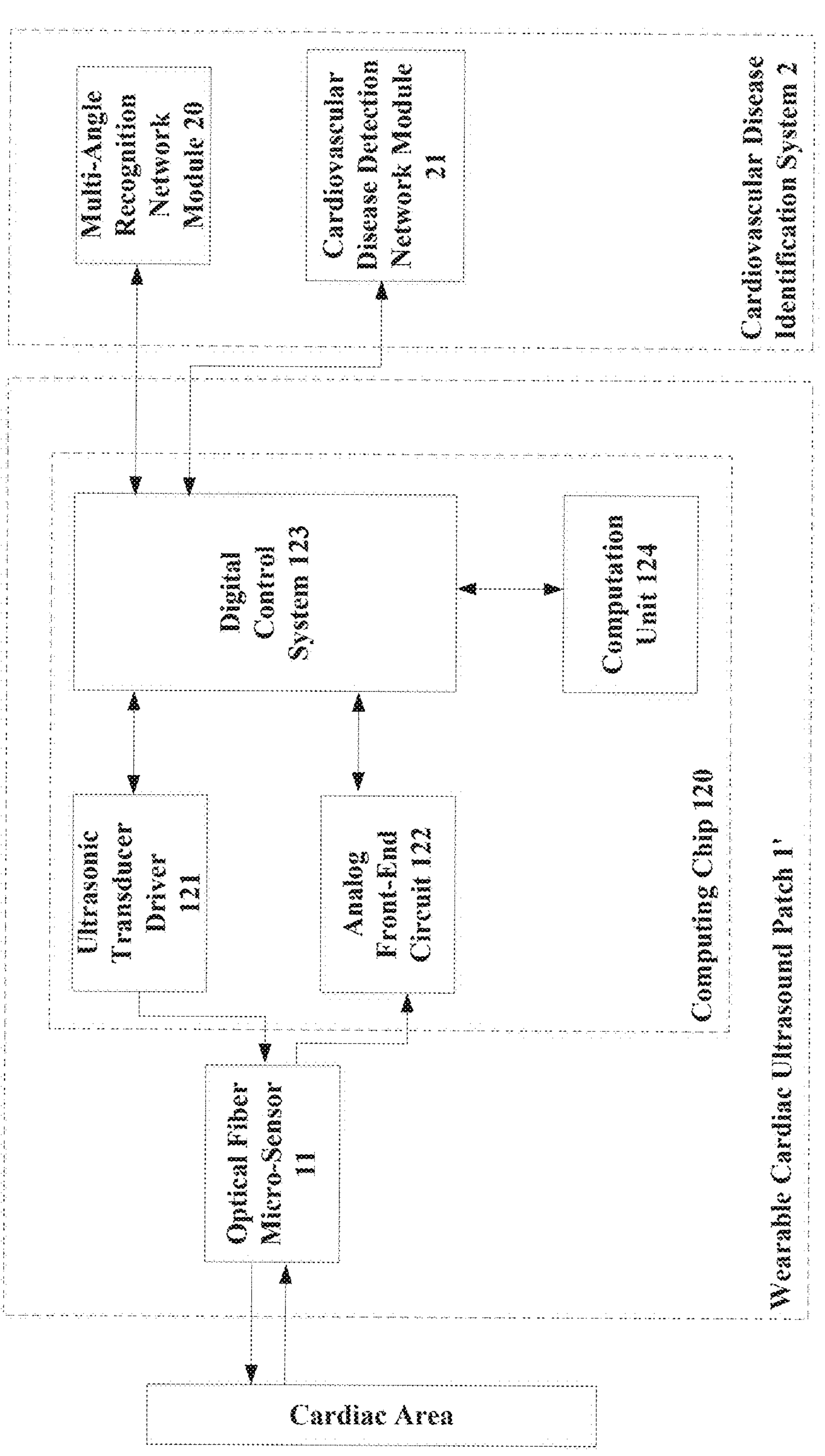
FIG. 5 is a basic block diagram illustrating the data transmission and processing between the cardiovascular disease identification system and the wearable cardiac ultrasound patch of the present invention.

Next, please refer to FIG. 5, which shows the basic block diagram of the data transmission and processing structure of the cardiovascular disease identification system of the present invention and the above-mentioned wearable cardiac ultrasound patch. As described above, the computing chip of the wearable cardiac ultrasound patch of the present invention comprises a data transmission function to transmit the raw data of the cardiac ultrasound images generated by the computing chip to the cardiovascular disease identification system 2. The cardiovascular disease identification system 2 comprises: a multi-angle identification network module 20 and a cardiovascular disease detection network module 21. The multi-angle identification network module 20 is used to perform cardiac ultrasound image reconstruction processing on the raw data of the cardiac ultrasound images to generate a cardiac ultrasound image to be identified, and the multi-angle identification network module stores multiple angle identification models, each of which contains at least one cardiac ultrasound image from a particular angle and the corresponding cardiac ultrasound image quality. Based on the cardiac ultrasound image to be identified, the corresponding angle identification model is selected to find the required cardiac ultrasound image and image quality for clinical diagnosis.

The aforementioned multiple angle identification models provide diverse information to enable the subsequent rapid and accurate examination of different structures and functions of the heart by doctors, avoiding blind spots caused by a single viewpoint. At the same time, combining multi-angle images can help with the diagnosis of heart diseases such as heart valve disease, cardiac defects, or cardiomyopathy, and also provide an assessment of cardiac function, aiding in the comprehensive analysis of cardiac contraction, relaxation function, and hemodynamics. The quality of the cardiac ultrasound image refers to the clarity, accuracy, and signal integrity of the heart image, which helps doctors make accurate diagnoses of the health of the heart and blood vessels. The quality of the cardiac ultrasound image is influenced by multiple factors, primarily comprising spatial resolution, contrast resolution, and depth penetration.

Therefore, the multi-angle identification network module 20 performs the aforementioned cardiac ultrasound perspective image or cardiac ultrasound image quality judgment on the cardiac ultrasound image to be identified after image reconstruction. If the cardiac ultrasound image to be identified does not meet the required cardiac ultrasound perspective image or cardiac ultrasound image quality, the computing chip drives each piezoelectric element to adjust the three-dimensional beamforming parameters for ultrasound transmission, in order to obtain raw data of the cardiac ultrasound images at different focus positions, and this process continues until the reconstructed cardiac ultrasound image based on the raw data of the subsequent images meets the required cardiac ultrasound perspective image and cardiac ultrasound image quality. The adjustment of the three-dimensional beamforming parameters comprises: adjusting the phase difference, amplitude difference between adjacent piezoelectric elements, and changing the delay time of the ultrasound transmission from the piezoelectric elements. Since the ultrasound beam can be controlled in different directions according to needs to achieve three-dimensional imaging, adjusting the phase difference and amplitude difference between adjacent piezoelectric elements can direct the beam to a specific direction. Moreover, the focal position affects the imaging depth and resolution, and changing the delay time of the piezoelectric element can focus the beam at different depths. As the wave phase changes over time, the phase describes the specific state (position) of the wave within its cycle. Therefore, phase difference and delay time are essentially interchangeable concepts in beamforming. The phase difference caused by delay time directly determines the direction and focusing ability of the beam. By adjusting these parameters, the angle and depth of the beam can be precisely controlled, thereby improving the accuracy and resolution of cardiac ultrasound imaging.

The cardiovascular disease detection network module 21 comprises a cardiac ultrasound signal database used to analyze the cardiac ultrasound images to be identified that meet the required cardiac ultrasound perspective image and cardiac ultrasound image quality, and to extract feature parameters from the analyzed images. Based on the cardiac ultrasound signal database and ultrasound algorithms, it performs classification of cardiac ultrasound images and cardiovascular diseases to generate a cardiovascular disease identification report. The feature parameters are numerical values extracted from the cardiac ultrasound images or data, which have specific diagnostic significance and can describe the anatomical structure and function of the heart. Common feature parameters include the size of heart chambers (e.g., left ventricular diameter, right atrial area), thickness of the heart wall (e.g., degree of myocardial hypertrophy), the shape and movement characteristics of heart valves (e.g., mitral valve opening area), the motion speed and pattern of the ventricular wall (regional myocardial motion disorder evaluation), blood flow velocity and volume, etc. These parameters quantitatively describe the health status or pathological changes of the heart, and serve as important criteria for disease diagnosis and prediction. The cardiac ultrasound algorithm is a series of computational methods based on data and image processing technologies aimed at extracting useful features from ultrasound images and performing analysis, enabling classification of cardiac ultrasound images and cardiovascular diseases. The cardiac ultrasound algorithm comprises the following processes: (1) enhancing image contrast and edge clarity to facilitate heart structure segmentation; (2) feature extraction, using machine learning or deep learning methods to automatically identify and quantify cardiac structure and function parameters from images; (3) data matching: comparing the extracted features with the cardiac ultrasound signal database, which contains a large number of labeled normal and pathological samples to help the cardiac ultrasound algorithm identify cardiovascular diseases; (4) disease diagnosis: classifying cardiac ultrasound images and cardiovascular diseases based on the abnormal patterns of feature parameters to generate diagnostic reports, for example, determining the presence of valve stenosis or myocardial ischemia. Therefore, the cardiovascular disease detection network module 21, by combining feature parameters and cardiac ultrasound algorithms, can significantly reduce diagnostic errors caused by human factors. On the other hand, the cardiac ultrasound algorithm can generate personalized reports based on the characteristics of the subject, offering individualized disease assessments and treatment suggestions. By continuously collecting and analyzing data, the cardiac ultrasound algorithm can monitor disease progression and assess treatment effects. This combination of technologies not only improves diagnostic efficiency but also enhances the clinical application value of medical imaging.

Figure 6:
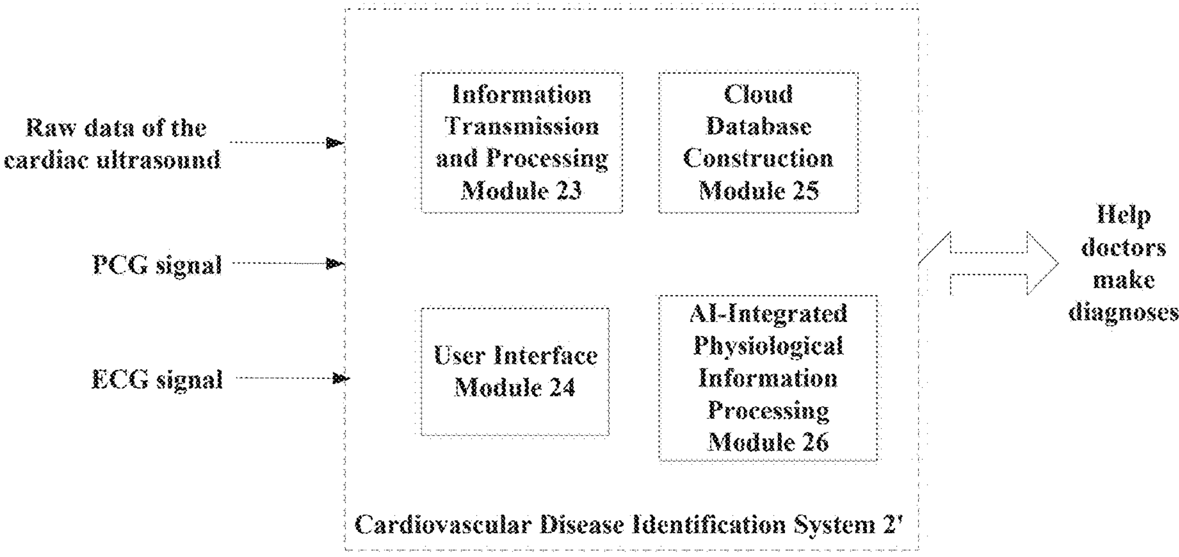
FIG. 6 is a system basic block diagram of another embodiment of the cardiovascular disease identification system of the present invention.

Cardiac ultrasound is primarily used for assessing cardiac structure and dynamic function, such as heart chamber size, myocardial motion, and valve function. However, cardiac ultrasound cannot provide direct information on the details of the heart's electrical activity. Therefore, the cardiovascular disease identification system of the present invention can also receive PCG (Phonocardiography) signals and ECG (Electrocardiography) signals sent separately from PCG and ECG detection devices. The ECG signals can clearly reflect the heart's electrophysiological activity, which is highly sensitive for diagnosing arrhythmias, myocardial ischemia, and infarction. The PCG signals, by recording heart sounds, can detect abnormal sounds in the early stages of certain valve diseases (such as stenosis or regurgitation). The data from the cardiac ultrasound, PCG signals, and ECG signals can mutually verify each other, improving the detection rate of comprehensive cardiovascular diseases, and assisting doctors in making more accurate diagnoses. As shown in FIG. 6, this is a basic block diagram of another embodiment of the cardiovascular disease identification system of the present invention. The cardiovascular disease identification system 2' in this embodiment comprises: an information transmission and processing module 23, a user interface module 24, a cloud database construction module 25, and an AI-integrated physiological information processing module 26.

The information transmission and processing module 23 is used to process the received raw data of cardiac ultrasound, PCG signals, and ECG signals, and perform signal processing, such as feature extraction. In the case of raw cardiac ultrasound data, this module comprises the processing of the multi-angle identification network module 20 shown in FIG. 5, i.e., used for performing cardiac ultrasound image reconstruction processing. As for the PCG and ECG signals, they are time-series signals rather than image data, so the information transmission and processing module 23 ensures the accurate synchronization of the PCG and ECG signals, especially when performing multimodal diagnosis. In some cases, these signals can be converted into image form to be combined with cardiac ultrasound images to enhance diagnostic effectiveness. Notably, in this embodiment, the subject of the cardiovascular disease identification system 2' is equipped not only with the wearable cardiac ultrasound patch but also with PCG and ECG patches for sensing, with the sensed PCG and ECG signals being sent to the cardiovascular disease identification system 2'.

The user interface module 24 is used to display the results processed by the information transmission and processing module 23, and to generate related parameters and data, while also marking abnormal signals for medical personnel to interpret.

The cloud database construction module 25 builds a cardiac ultrasound image database, PCG database, and ECG database to store the cardiac ultrasound images, PCG signals, and ECG signals input into the cardiovascular disease identification system 2' for further processing by the doctor. This processing may include verifying abnormal markers through the user interface module 24, such as marking four types of diseases: heart valve disease, congestive heart failure, coronary artery disease, and arrhythmia developed earlier, and developing a cardiovascular disease identification model using the data and marked content stored in the cardiac ultrasound image, PCG, and ECG databases.

The AI-integrated physiological information processing module 26 automatically analyzes the data, identifying common heart abnormalities such as arrhythmia, atrial fibrillation, tachycardia, heart valve disease, heart failure, and coronary artery disease to assist in medical diagnosis. Since physiological information comprises ECG and PCG signals, it can be used to establish an artificial intelligence cardiovascular disease identification model to combine relevant disease parameters with various neural networks (such as Convolution Neural Networks (CNN), Recurrent Neural Networks (RNN), transformer networks, generated AI networks) and AI technologies for classifying cardiovascular diseases, identifying heart valve disease, heart failure, coronary artery disease, and arrhythmia, and automatically assisting in disease prediction to reduce diagnostic time and misjudgment. Through this identification model, the system aids in the relevant analysis of cardiac ultrasound, ECG, and PCG signals, with the expectation that the model will be able to predict and identify the four cardiovascular diseases using just ECG and PCG, two relatively easy-to-detect physiological parameters.

Next, please refer to FIG. 7, which illustrates the processing flow diagram of the cardiovascular disease identification method of the present invention. The cardiovascular disease identification method of the present invention applies the aforementioned wearable cardiac ultrasound patch for cardiovascular disease identification processing. This wearable cardiac ultrasound patch transmits data to a cardiovascular disease identification system for processing, enabling cardiovascular disease identification. The cardiovascular disease identification method starts with step S1, where the computing chip of the wearable cardiac ultrasound patch transmits the raw data of the generated cardiac ultrasound images to the cardiovascular disease identification system, then proceeds to step S2.

In step S2, the cardiovascular disease identification system receives the raw data of the cardiac ultrasound image transmitted by the computing chip and performs cardiac ultrasound image reconstruction to generate a cardiac ultrasound image for identification, then proceeds to step S3.

In step S3, the cardiovascular disease identification system determines whether the cardiac ultrasound image for identification meets the clinical diagnostic requirements for the required cardiac ultrasound perspective image and cardiac ultrasound image quality. If it is determined that the cardiac ultrasound image to be identified does not meet the cardiac ultrasound perspective image or cardiac ultrasound image quality requirements, the system proceeds to step S4; otherwise, if the image meets the cardiac ultrasound perspective image or cardiac ultrasound image quality requirements, the system proceeds to step S5. The multiple-angle recognition models provide diverse information to facilitate the doctor's ability to quickly and accurately check the different structures and functions of the heart, avoiding blind spots from a single viewpoint. At the same time, combining multi-angle images helps confirm a heart disease diagnosis. The quality of the cardiac ultrasound image refers to the clarity, accuracy, and signal integrity of the heart image, which will assist the doctor in accurately diagnosing the health of the heart and blood vessels.

In step S4, if the cardiovascular disease identification system determines that the cardiac ultrasound image does not meet the required clinical diagnostic angle or quality, the computing chip drives the piezoelectric elements to adjust the parameters of the 3D beamforming ultrasound to transmit the ultrasound signal, generating raw data for cardiac ultrasound images with different focal points, then returns to step S2. In short, this continues until the reconstructed cardiac ultrasound image for identification, generated from the subsequent raw data transmitted from the computing chip, meets the required cardiac ultrasound perspective image or cardiac ultrasound image quality.

In step S5, the cardiovascular disease identification system analyzes the cardiac ultrasound image that meets the required cardiac ultrasound perspective image or cardiac ultrasound image quality and extracts feature parameters from the analyzed image. Based on a cardiac ultrasound signal database and cardiac ultrasound algorithms, it performs cardiac ultrasound image and cardiovascular disease classification, providing a cardiovascular disease identification report for the doctor's reference to reduce diagnosis time and misjudgments. On the other hand, the cardiovascular disease identification report can also provide personalized disease assessments and treatment suggestions, dynamically monitoring the patient's condition to improve diagnostic efficiency.

Figure 8:
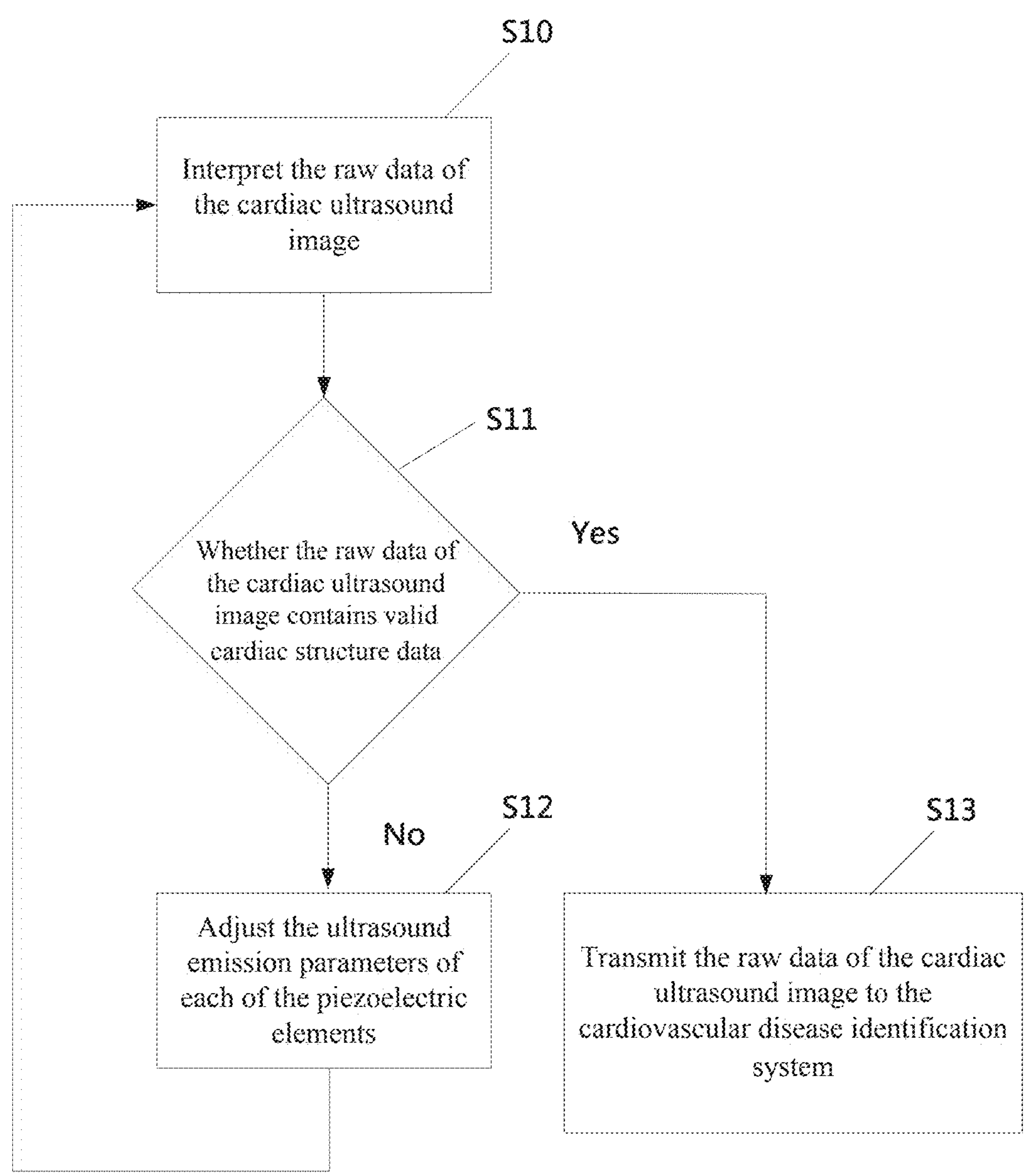
FIG. 8 is a flowchart illustrating the processing of raw data of cardiac ultrasound images in the cardiovascular disease identification method of the present invention.

The cardiovascular disease identification method of the present invention also includes processing the raw data of the cardiac ultrasound image generated by the computing chip of the wearable cardiac ultrasound patch, so that the cardiovascular disease identification system processes useful information from the raw data to avoid overloading the system's resources. As shown in FIG. 8, step S10 is first performed, where the computing chip of the wearable cardiac ultrasound patch interprets the raw data of the generated cardiac ultrasound image, then proceeds to step S11.

In step S11, after the interpretation, the computing chip analyzes whether the raw data of the cardiac ultrasound image contains valid cardiac structure data. If it does not, the system proceeds to step S12; if it does, it proceeds to step S13. The valid cardiac structure data refers to ultrasound echo information that clearly represents and reflects the cardiac structure (e.g., heart walls, valves, chambers, blood flow direction and speed, etc.) and related functions. This data will serve as the basis for subsequent reconstruction of the cardiac ultrasound image by the cardiovascular disease identification system.

In step S12, when the computing chip determines that the raw data of the cardiac ultrasound image does not contain valid cardiac structure data, it adjusts the ultrasound emission parameters of each piezoelectric element, such as frequency, focusing depth, or direction, and returns to step S10. This process repeats until the raw data generated from the computing chip contains valid cardiac structure data, ensuring the accuracy of the subsequent cardiac ultrasound image reconstruction by the cardiovascular disease identification system.

In step S13, when the computing chip determines that the raw data of the cardiac ultrasound image contains valid cardiac structure data, it transmits the raw data of the cardiac ultrasound image to the cardiovascular disease identification system for reconstruction.

In conclusion, the wearable cardiac ultrasound patch, cardiovascular disease identification system, and method of the present invention integrate the silicon photonic integrated circuit layer with the microelectromechanical integrated circuit layer into an optical fiber micro-sensor, which is then packaged together with the computing chip. This allows the patient to perform cardiac ultrasound detection in a convenient wearable manner, without the restrictions of time or location. Additionally, the various silicon photonic elements in the silicon photonic integrated circuit layer and the piezoelectric elements in the microelectromechanical integrated circuit layer are stacked and arranged in a two-dimensional array, enabling the wearable cardiac ultrasound patch to scan more angles. Furthermore, the cardiovascular disease identification system of the present invention can detect the patient's cardiac ultrasound, electrocardiography (ECG) signals, and phonocardiography (PCG) signals. After signal processing, cardiovascular disease-related parameters are obtained and used in artificial intelligence-based cardiovascular disease identification and diagnostic algorithms to classify diseases such as heart valve disease, heart failure, coronary artery disease, and arrhythmias. Computer automation is then used to assist in disease prediction, reducing the time and misjudgment of doctors in diagnosing cardiovascular diseases.

The examples above are only illustrative to explain principles and effects of the invention, but not to limit the invention. It will be apparent to those skilled in the art that modifications and variations can be made without departing from the spirit and scope of the invention. Therefore, the protection range of the rights of the invention should be as defined by the appended claims.

What is claimed is:

1. A wearable cardiac ultrasound patch for installing on the skin of the cardiac region to obtain cardiac images, the wearable cardiac ultrasound patch comprising:

an encapsulation body, one side of which is equipped with an adhesive layer for attaching to the skin of the cardiac region;

an optical fiber micro-sensor housed within the encapsulation body, the optical fiber micro-sensor comprising a silicon photonic integrated circuit layer with a plurality of silicon photonic elements arranged in a two-dimensional array and a microelectromechanical integrated circuit layer with multiple piezoelectric elements arranged in a two-dimensional array, and the silicon photonic integrated circuit layer and the microelectromechanical integrated circuit layer are vertically stacked, with each of the silicon photonic elements respectively corresponding to each of the piezoelectric elements, and the silicon photonic integrated circuit layer is arranged facing the adhesive layer, and the microelectromechanical integrated circuit layer is used to emit ultrasonic waves and propagate them to the cardiac region, when ultrasonic echoes act on each of the piezoelectric elements and cause material deformation, the material deformation is captured by the silicon photonic elements and converted into phase changes of optical signal, and the silicon photonic integrated circuit layer then outputs the electrical signal converted from the optical signal; and a computing chip housed within the encapsulation body, vertically stacked with the optical fiber micro-sensor, wherein the computing chip employs 3D beamforming technology to drive the each of the piezoelectric elements to emit ultrasound, digitizes the electrical signal output by the silicon photonic integrated circuit layer, and performs AI-based data analysis, allowing ultrasound beams to focus on different angles and depths of the heart, thereby obtaining multi-angle ultrasound data and generating raw data of the cardiac ultrasound image.

2. The wearable cardiac ultrasound patch of claim 1, wherein the computing chip comprises:

an ultrasonic transducer driver, supplying the required voltage and current to the plurality of piezoelectric elements of the microelectromechanical integrated circuit layer to control each of the piezoelectric elements to emit ultrasound;

an analog front-end circuit, used to amplify the electrical signal output by the silicon photonic integrated circuit layer, perform noise suppression, and filter to reduce noise, quantizes the electrical signal into digital signal through analog-to-digital conversion; and a digital control system, receiving the digital signal processed by the analog front-end circuit, performing digital signal processing and data analysis to generate raw data of the cardiac ultrasound image, and storing the raw data for subsequent cardiac ultrasound image reconstruction.

3. The wearable cardiac ultrasound patch of claim 2, wherein the computing chip further comprises: a computation unit for performing AI computation, interpretation, and identification on the raw data of the cardiac ultrasound image generated by the digital control system, when the raw data the cardiac ultrasound image lacks effective data on cardiac structure, the information feeds back to the digital control system to control the ultrasonic transducer driver in adjusting the parameters of each piezoelectric element for emitting ultrasound, so that the raw data of the cardiac ultrasound image generated by the digital control system comprises effective data of the cardiac structure, reflecting the image of the cardiac region to achieve accuracy in the subsequent reconstruction processing of the cardiac ultrasound image.

4. The wearable cardiac ultrasound patch of claim 2, wherein the digital control system further comprises data transmission capabilities for transmitting the raw data of the cardiac ultrasound image.

5. The wearable cardiac ultrasound patch of claim 4, further capable of transmitting data with an information processing device, wherein the digital control system transmits the generated raw data of the cardiac ultrasound image to the information processing device or receives control information from the information processing device, and the control information comprises adjustments to the power, frequency, and focusing methods of the ultrasonic transducer driver to optimize ultrasound parameter adjustments.

6. The wearable cardiac ultrasound patch of claim 1, wherein the computing chip performs an initialization operation during the first ultrasound emission by each of the piezoelectric elements for position calibration of the encapsulation body and the cardiac region, and the ultrasonic reflection data of the cardiac region contained by the raw data of the cardiac ultrasound image serves as the basis for position calibration, adjusting angles and depths to which the ultrasound beam emitted by each of the piezoelectric elements is focused on the heart.

7. The wearable cardiac ultrasound patch of claim 1, wherein the computing chip further comprises data transmission and storage functions for storing the raw data of the cardiac ultrasound image for subsequent reconstruction of the cardiac ultrasound image or transmitting the data to a cardiovascular disease identification system, and the cardiovascular disease identification system comprises a multi-angle identification network module and a cardiovascular disease detection network module, and the multi-angle identification network module stores multiple angle identification models for reconstructing the raw data of the cardiac ultrasound images to generate a cardiac ultrasound image to be identified and identifying the corresponding angle identification model to obtain the clinical diagnostic cardiac ultrasound perspective image and cardiac ultrasound image quality based on the cardiac ultrasound image to be identified, if the cardiovascular disease identification system determines that the cardiac ultrasound image to be identified does not meet the requirements of the cardiac ultrasound perspective image or cardiac ultrasound image quality, allowing the computing chip to drive each of the piezoelectric elements to adjust the ultrasound parameters of three-dimensional beamforming to emit ultrasound, thereby obtaining raw data of cardiac ultrasound images at different focal positions, and continue until the subsequently generated raw data produces a cardiac ultrasound image to be identified that meets the cardiac ultrasound perspective image and cardiac ultrasound image quality; the cardiovascular disease detection network module comprises a cardiac ultrasound signal database, which is used to analyze the cardiac ultrasound image to be identified that meets the cardiac ultrasound perspective image and cardiac ultrasound image quality, to extract feature parameters from the analyzed cardiac ultrasound image to be identified, and through the cardiac ultrasound signal database and cardiac ultrasound algorithm, performing cardiac ultrasound image and cardiovascular disease classification to provide a cardiovascular disease identification report.

8. A cardiovascular disease identification system, which can perform data transmission processing with the wearable cardiac ultrasound patch of claim 1, wherein the computing chip of the wearable cardiac ultrasound patch comprises a data transmission function to transmit the raw data of the cardiac ultrasound image generated by the computing chip to the cardiovascular disease identification system, the cardiovascular disease identification system comprising:

a multi-angle identification network module, configured to perform cardiac ultrasound image reconstruction processing on the raw data of the cardiac ultrasound image to generate a cardiac ultrasound image to be identified, wherein the multi-angle identification network module stores multiple view identification models, each of the view identification models comprises at least one cardiac ultrasound perspective image and corresponding cardiac ultrasound image quality, and identifies the corresponding view identification model based on the cardiac ultrasound image to be identified to obtain the cardiac ultrasound perspective image and cardiac ultrasound image quality required for clinical diagnosis, wherein if the cardiac ultrasound image to be identified does not meet the cardiac ultrasound perspective image or cardiac ultrasound image quality, the computing chip adjusts the three-dimensional beamforming ultrasound parameters to send ultrasound by driving each of the piezoelectric elements to obtain raw data of cardiac ultrasound images at different focal positions until the cardiac ultrasound image to be identified, obtained based on the subsequently generated raw data, meets the cardiac ultrasound perspective image and cardiac ultrasound image quality; and a cardiovascular disease detection network module, comprising a cardiac ultrasound signal database, configured to analyze the cardiac ultrasound image to be identified that meets the cardiac ultrasound perspective image and cardiac ultrasound image quality, extract feature parameters from the analyzed cardiac ultrasound image to be identified, and perform classification of the cardiac ultrasound image and cardiovascular diseases based on the cardiac ultrasound signal database and cardiac ultrasound algorithms to provide a cardiovascular disease identification report.

9. The cardiovascular disease identification system of claim 8, wherein the cardiovascular disease detection network module further comprises a heart sound signal database and receives sound signals generated by cardiac activities captured by a phonocardiography (PCG) detection device, analyzing and diagnosing the functionality and health condition of the heart based on the heart sound signal database.

10. The cardiovascular disease identification system of claim 8, wherein the cardiovascular disease detection network module further comprises an electrocardiography (ECG) signal database and receives electrocardiographic signals detected by an electrocardiography detection device, monitoring heart rhythms and diagnosing heart-related diseases based on the electrocardiography signal database.

11. The cardiovascular disease identification system of claim 8, wherein when the number of wearable cardiac ultrasound patches is three, each of the wearable cardiac ultrasound patches covers an emission range of 120 degrees, thereby achieving 360-degree cardiac ultrasound image, wherein the multi-angle identification network module uses the multiple view identification models to control the angle and depth of cardiac ultrasound emission via the computing chip.

12. A cardiovascular disease identification method applying the wearable cardiac ultrasound patch of claim 1, wherein the wearable cardiac ultrasound patch performs data transmission processing with a cardiovascular disease identification system to achieve cardiovascular disease identification, the cardiovascular disease identification method comprising the following steps:

(1) the computing chip of the wearable cardiac ultrasound patch transmits the raw data of the generated cardiac ultrasound image to the cardiovascular disease identification system;

(2) the cardiovascular disease identification system receives the raw data of the cardiac ultrasound image transmitted from the computing chip and performs cardiac ultrasound image reconstruction processing to generate a cardiac ultrasound image to be identified;

(3) the cardiovascular disease identification system determines whether the cardiac ultrasound image to be identified meets the cardiac ultrasound perspective image and cardiac ultrasound image quality required for clinical diagnosis, if the cardiac ultrasound image to be identified does not meet the cardiac ultrasound perspective image or cardiac ultrasound image quality, the computing chip adjusts the three-dimensional beamforming ultrasound parameters to send ultrasound by driving each of the piezoelectric elements to obtain raw data of cardiac ultrasound images at different focal positions until the cardiac ultrasound image to be identified, obtained based on the subsequently generated raw data, meets the cardiac ultrasound perspective image and cardiac ultrasound image quality; and (4) the cardiovascular disease identification system analyzes the cardiac ultrasound image to be identified that meets the cardiac ultrasound perspective image and cardiac ultrasound image quality, extracts feature parameters from the analyzed cardiac ultrasound image to be identified, and performs classification of the cardiac ultrasound image and cardiovascular diseases based on the cardiac ultrasound signal database and cardiac ultrasound algorithms to provide a cardiovascular disease identification report.

13. The cardiovascular disease identification method of claim 12, wherein when the number of wearable cardiac ultrasound patches installed on the skin in the cardiac region is three, respectively attached to the parasternal, apex, and subcostal regions, enabling each of the wearable cardiac ultrasound patches to cover an emission range of 120 degrees to achieve 360-degree cardiac ultrasound image.

14. The cardiovascular disease identification method of claim 12, wherein the ultrasound parameter comprises: adjusting the phase difference, amplitude difference between adjacent piezoelectric elements, and changing the delay time of the piezoelectric element emission.

15. The cardiovascular disease identification method of claim 12, wherein before performing step (1), the method further comprises the following steps:

(1-1) the computing chip of the wearable cardiac ultrasound patch interprets the raw data of the generated cardiac ultrasound image;

(1-2) the computing chip analyzes whether the interpreted raw data of the cardiac ultrasound image contains effective data of cardiac structures, wherein if it does not contain effective data of cardiac structures, proceed to step (1-3), and if it does, proceed to step (1-4);

(1-3) if the computing chip determines that the raw data of the cardiac ultrasound image does not contain effective data of cardiac structures, the computing chip adjusts the ultrasound emission parameter of each of the piezoelectric elements to ensure that the subsequent raw data of the cardiac ultrasound image generated by the computing chip contains effective data of the cardiac structure, and then proceed to step (1); and (1-4) if the computing chip determines that the raw data of the cardiac ultrasound image contains effective data of cardiac structures, proceed to step (1).

* * * * *